US00PP28749P2

(12) United States Plant Patent
Korlipara

(10) Patent No.: US PP28,749 P2
(45) Date of Patent: Dec. 5, 2017

(54) ***ECHINACEA* PLANT NAMED 'TNECHCMR'**

(50) Latin Name: ***Echinacea* spp.**
Varietal Denomination: TNECHCMR

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,204

(22) Filed: Aug. 22, 2016

(51) Int. Cl.
*A01H 5/02* (2006.01)

(52) U.S. Cl.
USPC ..... Plt./428

(58) Field of Classification Search
USPC ..... Plt./263.1, 428
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct *Echinacea* plant named 'TNECHCMR' characterized by raspberry-colored ray florets, enlarged dark raspberry-colored disc florets forming an anemone-type inflorescence, a multicrown, dwarf habit with upright strong stems, and excellent vigor.

1 Drawing Sheet

Botanical denomination: *Echinacea* spp.
Variety designation: 'TNECHCMR'.

BACKGROUND OF THE INVENTION

The present invention relates to a new and distinct cultivar of *Echinacea* and given the cultivar name 'TNECHCMR'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Cranberry Cupcake' (U.S. Plant Pat. No. 23,020), the new cultivar is shorter, with inflorescences that dark raspberry-colored rather than rose pink.

Compared to *Echinacea* 'Double Scoop Raspberry', (U.S. Plant Pat. No. 23,117), this new cultivar is much shorter, forms more crowns from the base, and has inflorescences that are a darker raspberry color.

This new *Echinacea* cultivar is uniquely distinguished by:

1. raspberry-colored ray florets,
2. enlarged dark raspberry-colored disc florets forming an anemone-type inflorescence,
3. a multicrown, dwarf habit with upright strong stems, and
4. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a nine-month-old *Echinacea* 'TNECHCMR' growing in the trial field in full sun in late July in Canby, Oreg.

FIG. 2 shows a close-up of the raspberry-colored ray florets.

DETAILED PLANT DESCRIPTION

The following is a detailed description of the new *Echinacea* cultivar based on observations of 18-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition, 2007.

Plant:

*Type.*—Herbaceous perennial.
*Hardiness.*—USDA Zones 4 to 9.
*Size.*—Grows to 80 cm wide and 50 cm tall to top of inflorescences.
*Form.*—Basal clump, with about 24 stems from the base.
*Vigor.*—Excellent.
*Roots.*—Fibrous, with many downward growing and few laterals, ivory in color, Yellow White 158D, roots develop easily from cuttings from the crown.

Leaf (stem):

*Type.*—Simple.
*Shape.*—Lanceolate.
*Arrangement.*—Alternate.

*Blade size*.—Grows to 11 cm long and 3.4 cm wide.

*Margins*.—Mostly entire.

*Apex*.—Acuminate.

*Base*.—Attenuate.

*Surface texture*.—Strigose on both sides.

*Venation*.—Pinnate, Yellow Green 145A on both sides, topside slightly tinted Greyed Purple 187A.

*Color*.—Topside Green N137A, bottom side closest to Yellow Green 147A.

*Petiole description*.—Clasping, grows to 4.5 cm long and 4 mm wide, scabrous, narrow leafy edges, topside Yellow Green 147D lightly tinted Greyed Purple 187A, bottom side Yellow Green 145A.

Inflorescence:

*Type*.—Composite on terminal stalked heads.

*Flowering stem*.—Grows to 45 cm tall from the base of the plant to the terminal inflorescence; unbranched to branched, with 1 to 24 inflorescences per stem; diameter growing to 10 mm wide near the inflorescence; strigose; Yellow Green 147B in shade, tinted 187A in sun.

*Size*.—Grows to 8 cm wide and 5.5 cm deep as disc enlarges.

*Form*.—Ray florets held slightly down, reflexing more in very old inflorescences, mature disc is conic.

*Immature inflorescence* (*bud*).—2.5 cm wide and 1.7 cm deep, ray florets held upright at a 70 degrees angle from vertical and rolled up so only the back color shows, Red Purple 63A except tip Greyed Yellow 160B, disc color Yellow Green 147A.

*Ray florets*.—Without pistil or stamen, number about 22 full size and 0 to 10 undersize, full size florets grow to 40 mm long and 11 mm wide, oblanceolate with the tip usually two-toothed (each acute), entire margins, base attenuate, glabrous on both sides; newly fully open florets topside closest to Red Purple 60A, bottom side Greyed Purple 186B; florets darken to topside Red Purple 59B, bottom side Red Purple 59A; fading when old.

*Disc*.—Flat becoming conic, becoming to 40 mm deep and 50 mm wide with maturity, overall color Red Purple 61A.

*Disc florets*.—To about 400 in number, each with 1 pistil and 4 stamen, grow to 22 mm long and 7 mm wide, each with one persistent bract (15 mm long with the top 3 mm colored Greyed Purple 187A on tip to 2 mm Yellow Green 148D blending to White NN155B); showy 4 to 5 lobed corollas to 18 mm long and 7 mm wide, tubular on the bottom with the lobes spread out like a fan, glabrous on both sides, back side color Red Purple 61A on lobes lightening to White NN155B at base, inside color Red Purple 59B on lobes lighten to 62A at base; pistil 10 mm long, ovary 4 mm long, White NN155A, style 5 mm long White NN155A, 2-branched stigma spreading 1.5 mm wide, Greyed Purple 187A; stamen 5 mm long, anthers 2.5 mm long and Greyed Purple N186A, filaments 2.5 mm long, White 155A, pollen none.

*Involucral bracts*.—In 4 leafy series, area grows to 32 mm wide and 12 mm deep, lobes lanceolate in shape, reflexed, grow to 14 mm long and 3 mm wide, Green 137A, margins strigose, tip acute, strigose on both sides.

*Receptacle*.—Grows to 15 mm wide and 18 mm deep, White NN155B.

*Bloom period*.—June through October in Canby, Oreg.

*Fragrance*.—Slight.

*Lastingness*.—Each inflorescence lasts about two weeks in Canby, Oreg.

Seeds: None.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

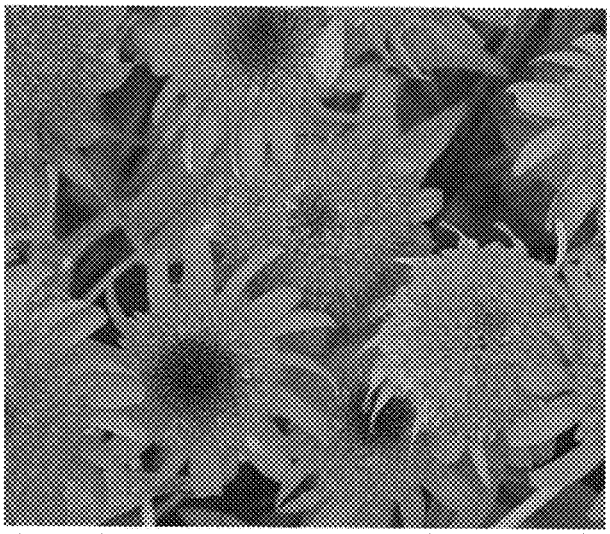

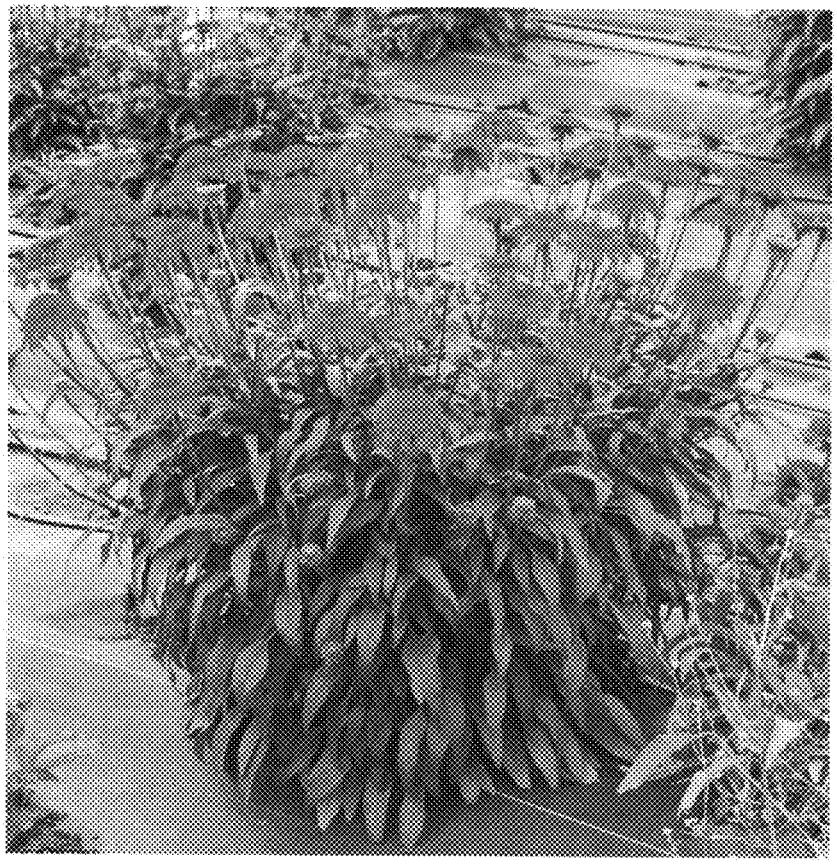
FIG. 1 above, FIG. 2 below